United States Patent [19]

Miyazawa et al.

[11] Patent Number: 5,110,346
[45] Date of Patent: May 5, 1992

[54] HERBICIDAL COMPOSITION AND METHOD FOR KILLING WEEDS USING THE SAME

[75] Inventors: Takeshige Miyazawa, Shizuoka; Kazuhiko Kawano, Niiza, both of Japan

[73] Assignee: Kumiai Chemical Industry Co., Ltd., Tokyo, Japan

[21] Appl. No.: 686,472

[22] Filed: Apr. 17, 1991

[30] Foreign Application Priority Data

May 12, 1990 [JP] Japan ................................ 2-122210

[51] Int. Cl.⁵ ...................... A01N 43/72; A01N 43/40
[52] U.S. Cl. ............................................. 71/90; 71/92
[58] Field of Search ........................................ 71/92, 90

[56] References Cited

U.S. PATENT DOCUMENTS 4,459,408 7/1984 Maulding et al. .................. 546/167
4,474,962 10/1984 Wepplo ............................... 546/167

FOREIGN PATENT DOCUMENTS 264489 1/1988 Japan .

*Primary Examiner*—Allen J. Robinson
*Assistant Examiner*—B. Bembenick
*Attorney, Agent, or Firm*—Oblon, Spivak, McClelland, Maier & Neustadt

[57] ABSTRACT

A herbicidal composition comprising (a) 9-(4-chloro-5-methoxycarbonylmethylthio-2-fluorophenyl)-8-thia-1,6-diazabicyclo[4.3.0]nonan-7-on and (b) 2-[4,5-dihydro-4-methyl-4-(1-methylethyl)-5-oxo-1H-imidazol-2-yl]-3-quinolinecarboxylic acid, 2-[4,5-dihydro-4-methyl-4-(1-methylethyl-5-oxo-1H-imidazol-2-yl]-5-ethyl-3-pyridinecarboxylic acid, its ester or its salt, as active ingredients.

8 Claims, No Drawings

HERBICIDAL COMPOSITION AND METHOD FOR KILLING WEEDS USING THE SAME

The present invention relates to a herbicidal composition, particularly a herbicidal composition having an excellent herbicidal effect on upland field, and a method for killing weeds.

It is disclosed in Japanese Unexamined Patent Publication No. 264489/1988 that 9-(4-chloro-5- methoxycarbonylmethylthio-2-fluorophenyl)-8-thia-1,6-diazabicyclo [4.3.0]nonan-7-on (hereinafter referred to as "Compound (I)") has a herbicidal activity. Also, 2-[4,5- dihydro-4-methyl-4-(1-methylethyl)-5-oxo-lH-imidazol-2yl]-3-quinolinecarboxylic acid (hereinafter referred to as "imazaquin") and 2-[4,5-dihydro-4-methyl-4-(1- methylethyl)-5-oxo-lH-imidazol-2-yl]-5-ethyl-3pyridinecarboxylic acid (hereinafter referred to as "imazethapyr") are generally known as a herbicide for a soybean field.

At present, many herbicides are used for upland field, but the types of weeds to be treated widely vary and their growing periods also range a long term. Thus, there is required a herbicide having such performances as a higher herbicidal effect, a herbicidal effect also on well grown weeds, a wide range of herbicidal spectrum and a high safety to crop plants.

We have studied and made a research on a herbicide which satisfies the above mentioned requirements, and found that a herbicidal composition comprising a mixture of (a) the compound (I) with (b) imazaquin or imazethapyr in an appropriate ratio achieves a herbicidal effect of killing various weeds, particularly of selectively killing a wide variety of weeds grown in a soybean field. The herbicidal composition of the present invention has many advantages that the herbicidal effect is synergistically improved over the case of using the respective active ingredients independently, that the herbicidal effect can be achieved at a dose of a small amount, that the herbicidal effect can be stably achieved also on well grown weeds and that the herbicidal effect can be achieved for a long range of period from the initial stage to the matured stage of growing.

That is, the present invention provides a herbicidal composition comprising (a) 9-(4-chloro-5-methoxycarbonylmethylthio -2-fluorophenyl)-8-thia-1,6diazabicyclo [4.3.0]nonan-7-on and (b) 2-[4,5-dihydro-4-methyl-4-(1-methylethyl)-5-oxo-lH-imidazol-2-yl]-3quinolinecarboxylic acid or 2-[4,5-dihydro-4-methyl-4-(1methylethyl) 5-oxo-lH-imidazol-2-yl]-5-ethyl-3pyridinecarboxylic acid, as active ingredients (hereinafter referred to as "the composition of the present invention").

The compound (I), imazaquin and imazethapyr used as the active ingredients in the composition of the present invention respectively have the chemical structures as shown in the following Table 1, but the imazaquin and the imazethapyr can be used in the form of an ester or a salt such as ammonium salt.

TABLE 1

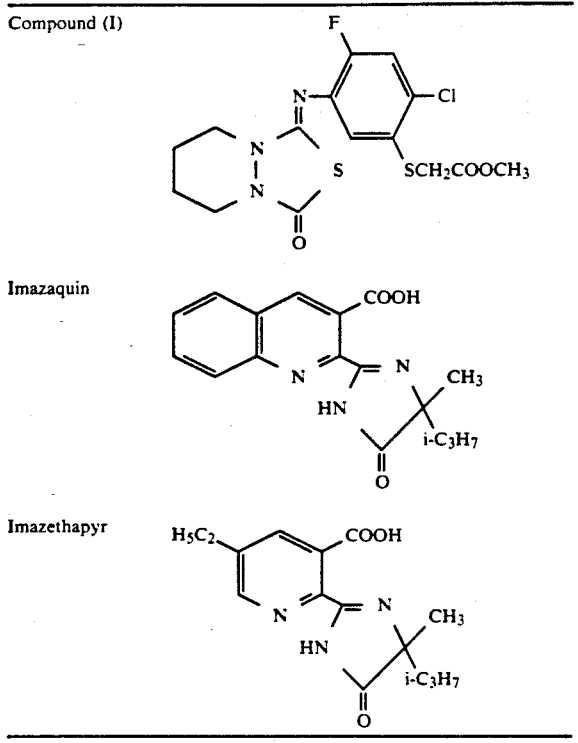

Examples of weeds to be treated with the composition of the present invention include broadleaf weeds such as morningglory (*Ipomoea* sp.), pigweed (*Amaranthus* sp.), common lambsquarters (*Chenopodium album*), common cocklebur (*Xanthum strumarium*), hemp sesbania (*Sesbania exaltata*), velvetleaf (*Abutilon theophrasti*), sicklepod (*Cassia obtusifolia*), prickly sida (*Sida spinosa*), field bindweed (*Convolvulus arvensis*), shepherdspurse (*Capsella bursa-pastoris*), common purslane (*Portulaca oleracea*), black nightshade (*Solanum niqrum*), annual sowthistle (*Sonchus oleraceus*), smartweed (*Polyqonum* sp.), wild sunflower (*Helianthus sp.*), hairy beggarticks (*Bidens pilosa*), and the like; and gramineous weeds such as barnyardgrass (*Echinochloa sp.*), foxtail (*Setaria*sp.), crabgrass (*Diqitaria* sp.), johnsongrass (*Sorqhum halepense*), goosegrass (*Eleusine sp.*), and the like.

The composition of the present invention is particularly suitable for killing weeds at the same time, such as hemp sesbania, prickly sida, morningglory, velvetleaf, and common cocklebur, the growth of which is hardly controllable.

The composition of the present invention can be applied to various plants in various ways, but is particularly suitable for foliage treatment in a soybean field.

The herbicidal composition of the present invention is used generally in previously mixed formulation, but each of the active ingredients may be mixed in site at the time of application.

The mixing ratio of (a) the compound (I) with (b) imazaquin or imazethapyr used as the active ingredients of the present invention may vary widely, but the imazaquin or the imazethapyr may be mixed in an amount of from 2 to 50 parts by weight, preferably from 2 to 35 parts by weight per part by weight of the compound (I).

When the composition of the present invention is applied as a herbicide, the active ingredient may be applied in various formulations depending on its use object, which are commonly used as herbicidal compositions, such as a wettable powder, a flowable agent, a granule, an emulsifiable concentrate or a dust by blending it with an inert liquid or a solid carrier, a surfactant, a dispersing agent or an adjuvant which is commonly employed for the formulation of agricultural chemicals.

For instance, a typical example of a wettable powder formulation comprises from 1 to 60% by weight of the total amount of active ingredients, from 1 to 5% by weight of a surfactant and from 35 to 98% by weight of the remainder including a carrier and the like.

As the carrier to be used for the formulation, there may be enumerated a solid carrier such as Jeeklight, talc, bentonite, clay, kaolin, diatomaceous earth, white carbon, vermiculite, slaked lime, silica sand, ammonium sulfate and urea, or a liquid carrier such as isopropyl alcohol, xylene, cyclohexanone, methyl naphthalene, acetone, isophorone, dimethylsulfoxide, acetonitrile, vegetable oil and water. As the surfactant and dispersing agent, there may be enumerated, for example, an alcohol-sulfuric acid ester, an alkylaryl sulfonate, lignin sulfonate, a polyoxyethylene glycol ether, a polyoxyethylene alkylaryl ether and a polyoxyethylene sorbitol mono-alkylate. As the adjuvant, for example, carboxymethylcellulose, polyethylene glycol and gum arabic may be enumerated. The herbicide may be dilluted to a suitable concentration before application, or may directly be applied.

The herbicide of the present invention is capable of controlling various weeds in an agricultural field such as an upland field or an orchard, or in a forest, a lawn or other non-agricultural field by soil treatment before or after the emergence of weeds or by foliage treatment. Further, the herbicide is capable of controlling various weeds in a paddy field by irrigated soil treatment before or after the emergence of weeds or by foliage treatment.

If desired, the compound of the present invention may be used in combination with insecticides, sterilizers, other herbicides, plant growth controlling agents, fertilizers or the like.

The amount of the composition of the present invention to be applied may vary depending on the types of crops and weeds to be treated, the weather conditions, the types of formulations, the mixing ratio of the active ingredients, the application method, the application site, timing, etc., but it is applied generally in a dose of from 10 to 200 g, preferably from 20 to 150 g of the total active ingredients per hectare (ha).

Now, the formulations of the composition of the present invention will be described in detail with reference to typical Formulation Examples, but the present invention should not be limited thereto. In the following Formulation Examples, "%" means "% by weight".

FORMULATION EXAMPLE 1 (Wettable powder)

2% of Compound (I), 25% of imazaquin, 1% of surfactant (polyoxyethylenealkylarylether and alkylarylsulfonate) and 72% of fine talc were uniformly mixed and pulverized to obtain a wettable powder.

FORMULATION EXAMPLE 2 (Wettable powder)

4% of Compound (I), 20% of imazethapyr, 2% of surfactant (polyoxyethylenealkylarylether and alkylarylsulfonate) and 74% of fine clay were uniformly mixed and pulverized to obtain a wettable powder.

The herbicidal effects of the composition of the present invention will be described with reference to Test Examples. The herbicidal effects were evaluated by growth-inhibiting rate (%) determined by measuring the total weight of the part above the earth of plants to be treated and calculating according to the following equation.

Growth-inhibiting Rate (%) =

$$\left( 1 - \frac{\text{total weight of part above the earth of treated plants}}{\text{total weight of part above the earth of non-treated plants}} \right) \times 100$$

TEST EXAMPLE 1 (Foliage treatment in upland field)

Into a 800 cm² pot, soil was filled, and seeds of morningglory (Ipo), common cocklebur (Xan), hemp sesbania (Ses), prickly sida (Sid) and soybean (Gly) were sown and covered with soil to a depth of 0.5–1 cm. The seeds were grown in a glass chamber at 15–25° C. for 3 weeks. Thereafter, a wettable powder (containing the active ingredients as shown in the following Table 2) formulated in accordance with Formulation Example 1 was diluted with water in an amount of 250 liters/ha and uniformly applied to the foliage of the plants from above by a small size sprayer at such a dose of the active ingredient as indicated in the following Table 2. At this stage, the soybean was grown to the 1.5 leaf stage, and the remaining common cocklebur, morningglory, hemp sesbania and prickly sida were grown to 1–3 leaf stages. After the application, the pot was left in the glass chamber for 30 days, and the herbicidal effects and the phytotoxicity were evaluated. The results are shown in the following Table 2.

TABLE 2

| Compound applied | Dose of active ingredient (g/ha) | Herbicidal effect | | | | Phytotoxicity |
|---|---|---|---|---|---|---|
| | | Ipo | Xan | Ses | Sid | Gly |
| Compound (I) (Comparative Example 1) | 2.5 | 33 | 60 | 7 | 14 | nil |
| | 5.0 | 76 | 83 | 24 | 34 | nil |
| | 10.0 | 88 | 95 | 43 | 72 | nil |
| Imazaquin (Comparative Example 2) | 30.0 | 72 | 87 | 8 | 13 | nil |
| | 60.0 | 95 | 94 | 25 | 41 | nil |
| | 120.0 | 98 | 96 | 52 | 74 | nil |
| Compound (I) + Imazaquin (Test Example 1) | 2.5 + 30.0 | 98 | 100 | 18 | 37 | nil |
| | 2.5 + 60.0 | 100 | 100 | 45 | 63 | nil |
| | 2.5 + 120.0 | 100 | 100 | 65 | 94 | nil |
| | 5.0 + 30.0 | 100 | 100 | 33 | 55 | nil |
| | 5.0 + 60.0 | 100 | 100 | 55 | 88 | nil |
| | 5.0 + 120.0 | 100 | 100 | 78 | 100 | nil |
| | 10.0 + 30.0 | 100 | 100 | 65 | 85 | nil |
| | 10.0 + 60.0 | 100 | 100 | 79 | 98 | nil |
| | 10.0 + 120.0 | 100 | 100 | 93 | 100 | nil |

COMPARATIVE EXAMPLE 1

The same procedure as in Test Example 1 was repeated, except that Compound (I) was used alone as an active ingredient.

COMPARATIVE EXAMPLE 2

The same procedure as in Test Example 1 was repeated, except that imazaquin was used alone as an active ingredient.

TEST EXAMPLE 2 (Foliage treatment in upland field)

Into a 800 cm$^2$ pot, soil was filled, and seeds of morningglory (Ipo), common cocklebur (Xan), hemp sesbania (Ses), prickly sida (Sid) and soybean (Gly) were sown and covered with soil to a depth of 0.5–1 cm. The seeds were grown in a glass chamber at 15–25° C. for 30 days. Thereafter, a wettable powder (containing the active ingredients as shown in the following Table 3) formulated in accordance with Formulation Example 1 was diluted with water in an amount of 250 liters/ha and uniformly applied to the foliage of the plants from above by a small size sprayer at such a dose of the active ingredient as indicated in the following Table 3. At this stage, the soybean was grown to the 4 leaf stage, and the remaining common cocklebur, morningglory, hemp sesbania and prickly sida were grown to 3–7 leaf stages. After the application, the pot was left in the glass chamber for 30 days, and the herbicidal effects and the phytotoxicity were evaluated. The results are shown in the following Table 3.

TABLE 3

| Compound applied | Dose of active ingredient (g/ha) | Herbicidal effect | | | | Phytotoxicity |
|---|---|---|---|---|---|---|
| | | Ipo | Xan | Ses | Sid | Gly |
| Compound (I) | 5.0 | 13 | 16 | 38 | 5 | nil |
| (Comparative Example 1) | 10.0 | 21 | 86 | 70 | 14 | nil |
| Imazethapyr | 30.0 | 27 | 78 | 22 | 2 | nil |
| (Comparative Example 3) | 60.0 | 35 | 90 | 36 | 6 | nil |
| | 120.0 | 52 | 96 | 48 | 15 | nil |
| Compound (I) + Imazethapyr (Test Example 2) | 5.0 + 30.0 | 75 | 98 | 73 | 34 | nil |
| | 5.0 + 60.0 | 81 | 100 | 82 | 40 | nil |
| | 5.0 + 120.0 | 86 | 100 | 100 | 47 | nil |
| | 10.0 + 30.0 | 90 | 100 | 96 | 51 | nil |
| | 10.0 + 60.0 | 92 | 100 | 100 | 64 | nil |
| | 10.0 + 120.0 | 95 | 100 | 100 | 68 | nil |

COMPARATIVE EXAMPLE 3

The same procedure as in Test Example 1 was repeated, except that imazethapyr was used alone as an active ingredient.

We claim:

1. A herbicidal composition comprising (a) 9-(4-chloro-5-methoxycarbonylmethylthio-2-fluorophenyl)-8-thia-1,6diazabicyclo[4.3.0]nonan-7-on and (b) 2-[4,5-dihydro-4-methyl-4-(1-methylethyl)-5-oxo-1H-imidazol-2-yl]-3quinolinecarboxylic acid, or 2-[4,5-dihydro 4-methyl-4-(1- methylethyl)-5-oxo-1 H-imidazol-2-yl]-5-ethyl-3-pyridinecarboxylic acid, its ester or its salt, as active ingredients.

2. The herbicidal composition according to claim 1, wherein the mixing weight ratio of the former ingredient (a)/the latter ingredient (b) is.1/2–50.

3. The herbicidal composition according to claim 1, wherein the mixing weight ratio of the former ingredient (a)/the latter ingredient (b)is 1/2–35.

4. The herbicidal composition according to claim 1, wherein the composition is in the form of a wettable powder comprising from 1 to 60% by weight of the total amount of the active ingredients, from 1 to 5% by weight of a surfactant or a dispersing agent and from 35 to 98% by weight of a carrier or adjuvant.

5. A method for killing weeds, which comprises applying synergistic crop safe a herbicidally effective amount of the herbicidal composition as claimed in claim 1 to an upland field.

6. The method according to claim 5, wherein the upland field is a soybean field.

7. The method according to claim 5, wherein the herbicidal composition is applied in an amount of from 10 to 200 g of the active ingredients per hectare.

8. The method according to claim 5, wherein the herbicidal composition is applied in an amount of from 20 to 150 g of the active ingredients per hectare.

* * * * *

UNITED STATES PATENT AND TRADEMARK OFFICE
CERTIFICATE OF CORRECTION

PATENT NO. : 5,110,346
DATED : May 5, 1992
INVENTOR(S) : Takeshige MIYAZAWA, et al.

It is certified that error appears in the above-identified patent and that said Letters Patent is hereby corrected as shown below:

In the Abstract, lines 1-3;

Column 1, lines 11-13;

Column 1, lines 52-54;and at

Column 6, lines 7-9;

reads:
"9-(4-chloro-5-methoxycarbonylmethylthio-2-fluorophenyl)-8-thia-1,6-diazabicyclo[4.3.0]nonan-7-on"

should read:
--9-(4-chloro-2-fluoro-5-methoxycarbonylmethylthiophenylimino)-8-thia-1,6-diazabicyclo [4.3.0]nonane-7-one--.

UNITED STATES PATENT AND TRADEMARK OFFICE
CERTIFICATE OF CORRECTION

PATENT NO. : 5,110,346
DATED : May 5, 1992
INVENTOR(S) : Takeshige Miyazawa, et al It is certified that error appears in the above-indentified patent and that said Letters Patent is hereby corrected as shown below:

Col. 6, claim 1, line 1, after the word comprising, insert a synergistic, crop safe, herbicidally effective amount of.

Signed and Sealed this

Twenty-fourth Day of August, 1993

Attest:

BRUCE LEHMAN

Attesting Officer

*Commissioner of Patents and Trademarks*

UNITED STATES PATENT AND TRADEMARK OFFICE
CERTIFICATE OF CORRECTION

PATENT NO. : 5,110,346
DATED : May 5, 1992
INVENTOR(S) : Takeshige MIYAZAWA, et al.

It is certified that error appears in the above-indentified patent and that said Letters Patent is hereby corrected as shown below:

TITLE PAGE:

In the Abstract, line 6, "yl-4-(1-methylethyl-5-oxo)"

should read --yl-4-(1-methylethyl)-5-oxo--.

Col 1, line 20, reads "3pyridinecarboxylic";

should read --3-pyridinecarboxylic--.

Col. 1, line 56, reads "3quinolinecarboxylic";

should read --3-quinolinecarboxylic--.

Col. 1, line 57, reads "(1methylethyl)5-oxo";

should read --(1-methylethyl)-5-oxo--.

Col. 1, line 58, "3pyridinecarboxylic";

should read --3-pyridinecarboxylic--.

Col. 6, line 10, "dihydro-4-methyl-4-((1-methylethyl)"

should read --dihydro-4-methyl-4-(1-methylethyl)--.

UNITED STATES PATENT AND TRADEMARK OFFICE
CERTIFICATE OF CORRECTION

PATENT NO. : 5,110,346
DATED : May 5, 1992
INVENTOR(S) : Takeshige MIYAZAWA, et al.

It is certified that error appears in the above-indentified patent and that said Letters Patent is hereby corrected as shown below:

Col. 6, line 11, "3quinolinecarboxylic"

should read --3-quinolinecarboxylic--.

Col. 6, line 12, "dihydro 4-methyl"

should read --dihydro-4-methyl--.

Signed and Sealed this

Fourteenth Day of December, 1993

Attest:

BRUCE LEHMAN

Attesting Officer

Commissioner of Patents and Trademarks